United States Patent [19]

Hope

[11] Patent Number: Plant 5,593

[45] Date of Patent: Dec. 10, 1985

[54] IMPATIENS PLANT NAMED VISTA IMPATIENS NO. 3

[75] Inventor: Claude Hope, Cartago, Costa Rica

[73] Assignee: Pan American Plant Company, Parrish, Fla.

[21] Appl. No.: 566,803

[22] Filed: Dec. 29, 1983

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Schwartz, Jeffery, Schwaab, Mack, Blumenthal & Koch

[57] ABSTRACT

A new and distinct cultivar of impatiens Plant known by as Vista Impatiens No. 3, and particularly characterized by its compact, spreading and self-branching habit; large and brilliant carmine flowers; dark red-green foliage, and suitably for growing as a bedding plant, pot plant or hanging basket.

1 Drawing Figure su

The present invention relates to a new and distinctive cultivar of impatiens plant, botanically known as Impatiens, and known by the cultivar name Vista Impatiens No. 3.

This new cultivar was the result of a planned program of hybridization the purpose of which was to obtain a series of plants having a wide range of colors and with very large flowers derived from the New Guinea complex of species collected by the Longwood Garden Expedition of 1970. The new cultivar was selected in 1981, and given seedling No. 3381-57-2. The cultivar was produced by crossing seedlings 3081-1×3357-1.

Asexual reproduction by terminal or stem cuttings taken by me at Cartago, Costa Rica has shown that the unique features of this new impatiens are stabilized and are reproduced true to type in sucessive propagations.

The following characteristics distinguish the new impatiens from both its parent cultivar and other cultivated Impatiens of this type known and used in the floriculture industry:

1. Vista Impatiens No. 3 was selected for its compact growing habit, making it suitable for growing as bedding plants, pot plant culture and hanging baskets.

2. Flower size is consistently large (60 mm. ), and the flower color is a brilliant carmine red.

3. The foliage color is dark red green, providing a beautiful background and contrast to the flowers.

4. Excellent self-branching habit.

5. Exhibits good keeping quality in both having baskets and pots outside in full sun (fall, winter and spring months), and under light shade in summer in Florida where it will bloom year-round in the absence of frost.

6. Growth rate is moderate, producing a low dome-shaped plant 38–45 cm. high and 45–60 cm. in diameter in 6–8 weeks in a 5½" pot.

The accompanying colored photograph illustrates the overall appearance of this cultivar, showing the colors as true as it is reasonably possible to obtain in a colored reproduction of this type.

The following is a detailed description of my new impatiens cultivar based on plants produced under commercial practice in Cortez and Parrish, Fla., grown outdoors in full sun during the fall, winter and spring months and uner light shade during the summer months. Color references are made to The Royal Horticultural Society Colour Chart except where general terms of ordinary dictionary significance are used.

Parentage: Seedling No. 3381-57-2, produced by crossing Seedling No. 3081-1 with Seedling No. 3357-1.

Propagation:

A. *Type cutting.*—Tip cuttings, with 5 cm. stems.

B. *Time to initiate roots.*—10–14 days at 27° C. summer, 12–16 days at 18° C. winter.

C. *Rooting habit.*—Abundant and fibrous.

Plant description:

A. *Form.*—Self-branching, spreading, compact, low dome-shaped plant.

B. *Habit of growth.*—Rate of growth moderate for this type of plant; vegetative shoots are formed at the lower nodes and flowers at the higher nodes.

C. *Foliage description.*—Lower leaves opposite, higher leaves in whorls; leaves are simple. 1. Size: Average full grown leaf is 150 mm. long×52 mm. wide. Full grown leaves have petioles 45 mm. long, young leaves have short 5–10 mm. petioles. 2. Shape: Elliptic, apex acute to slightly acuminate. 3. Texture: Smooth, glabrous. 4. Margin: Serrulate. 5. Color: young foliage, top side close to yellow green 147A but extremely shiney; underside close to greyed purple 183A; mature foliage, top side close to yellow green 147A; underside finely mottled green and grey red, 181B. 6. Venation: Pinnate, main vein infused with greyed red 181B.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperatures in Florida.

C. *Flower bud description.*—Conical, covered with three sepals. Upper sepals are 10 mm. long×6 mm. wide, apex acuminate; lower sepal is 14 mm. long×8 mm. wide, apex acuminate; upper sepals are green in color, lower sepal is colorless infused with green at the apex (apex green). A hollow spur (35 mm. long when full grown) is connected to lower sepal at the base. Spur is colorless infused with red.

D. *Flowers borne.*—On peduncles 60 mm. long, green in color.

E. *Quantity of flowers.*—One flower per leaf, occurring progressively around the whorl of leaves.

F. *Petals.*—(1) Shape: Top petal heart-shaped with a broad rounded base. All other petals heart-shaped with pointed bases. (2) Color, top side red 52A when opening, with a slight pinkish halo type of eye, fading to red 51A; underside red 52D. (3) Number of petals: Five; with the middle and lower petals slightly united at base on each side. (4) Size of flowers: Top petal 26 mm. long×35 mm. wide; 2 middle petals 30 mm. long×∞mm. wide; 2 lower petals 32 mm. long×34 mm. wide. Total flower diameter is 60 mm.

G. *Reproductive organs.*—(1) Stamens: Five in number, with the lower stamen being shorter than the others. Stamens united in an asymmetrical tube surrounding and covering the ovary. (a) Anther shape: Hooded, color, cream infused with red. (b) Pollen color, cream. (2) Pistils; (a) Stigma shape: Five pointed star, colorless. (b) Style color: Cream, very short. (c) Ovaries: 5, celled, size 5 mm; color green.

Disease resistance:

No general diseases noted. Insect problems can include the two-spotted spider mite which can cause foliar injury and thrips which can cause stunting and injury to the growing tip.

I claim:

1. A new and distinct cultivar of impatiens plant known as Vista Impatiens No. 3, as described and illustrated, and particularly characterized by its compact, spreading and self-branching habit; large and brilliant carmine flowers; dark red-green foliage, and suitability for growing as a bedding plant, pot plant or hanging basket.

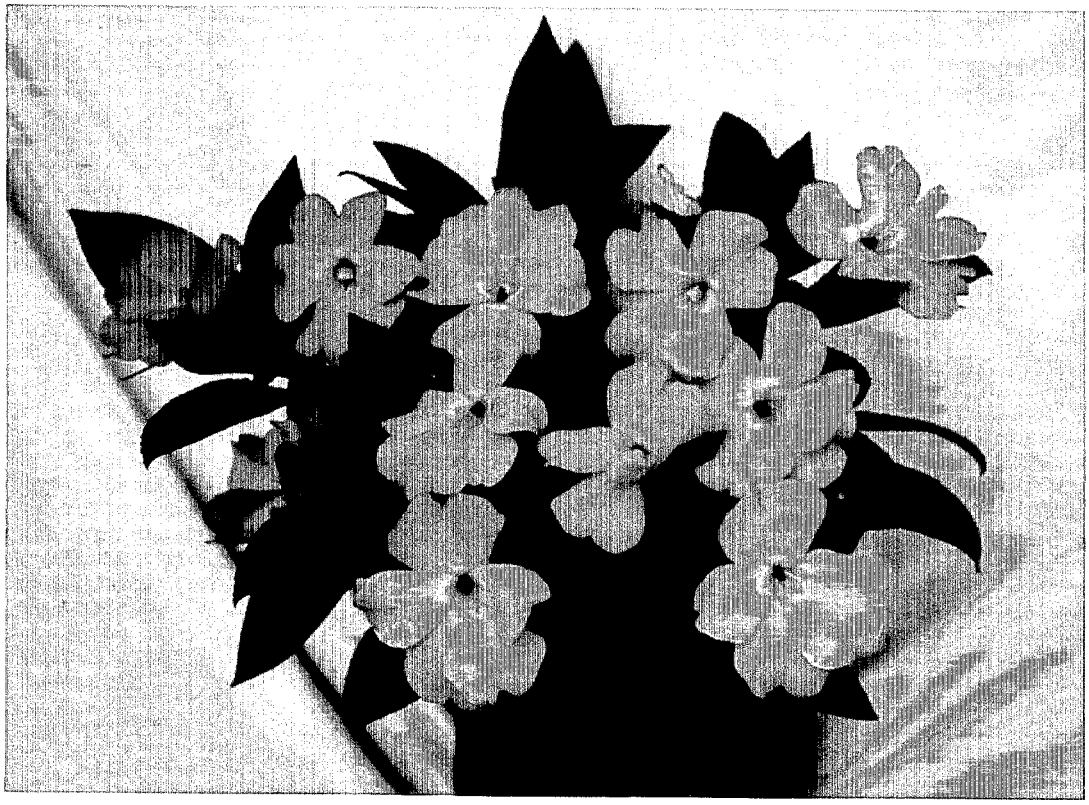

* * * * *